United States Patent
Graham

(10) Patent No.: US 7,378,389 B2
(45) Date of Patent: *May 27, 2008

(54) BOTULINUM TOXIN NEUROTOXIC COMPONENT FOR TREATING JUVENILE CEREBRAL PALSY

(75) Inventor: Herbert Kerr Graham, Melbourne (AU)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/752,096

(22) Filed: May 22, 2007

(65) Prior Publication Data

US 2007/0224221 A1 Sep. 27, 2007

Related U.S. Application Data

(63) Continuation of application No. 10/976,507, filed on Oct. 29, 2004, which is a continuation of application No. 10/155,280, filed on May 22, 2002, now abandoned, which is a continuation of application No. 08/211,352, filed as application No. PCT/GB92/01697 on Sep. 16, 1992, now Pat. No. 6,395,277.

(30) Foreign Application Priority Data

Sep. 24, 1991 (GB) ................. 9120306.7

(51) Int. Cl.
*A61K 38/00* (2006.01)
*A61K 39/00* (2006.01)
*C07K 14/33* (2006.01)

(52) U.S. Cl. .......... 514/2; 514/21; 424/184.1; 424/236.1; 424/247.1; 530/350

(58) Field of Classification Search .......... 514/2, 514/21; 424/184.1, 236.1, 247.1; 530/350
See application file for complete search history.

(56) References Cited

U.S. PATENT DOCUMENTS

| | | | |
|---|---|---|---|
| 2,373,454 A | 4/1945 | Burny et al. |
| 2,719,102 A | 9/1955 | Baldwin, Jr. |
| 3,132,995 A | 5/1964 | Berger et al. |
| 4,234,566 A | 11/1980 | Packman et al. |
| 4,713,240 A | 12/1987 | Wilkins et al. |
| 4,720,494 A | 1/1988 | Felger et al. |
| 4,832,936 A | 5/1989 | Holter et al. |
| 4,932,936 A | 6/1990 | Dykstra et al. |
| 4,935,969 A | 6/1990 | Farnsworth |
| 5,053,005 A | 10/1991 | Borodic |
| 5,055,291 A | 10/1991 | Lam et al. |
| 5,055,302 A | 10/1991 | Laties et al. |
| 5,056,291 A | 10/1991 | Leung |
| 5,183,462 A | 2/1993 | Borodic |
| 5,298,019 A | 3/1994 | Borodic |
| 5,401,243 A | 3/1995 | Borodic |
| 5,437,291 A | 8/1995 | Pasricha et al. |
| 5,512,547 A | 4/1996 | Johnson et al. |
| 5,562,907 A | 10/1996 | Arnon |
| 5,696,077 A | 12/1997 | Johnson et al. |
| 5,766,605 A | 6/1998 | Sanders et al. |
| 6,113,915 A | 9/2000 | Aoki et al. |
| 6,290,961 B1 | 9/2001 | Aoki et al. |
| 6,306,403 B1 | 10/2001 | Donovan |
| 6,319,505 B1 | 11/2001 | Aoki et al. |
| 6,333,037 B1 | 12/2001 | Aoki et al. |
| 6,372,226 B2 | 4/2002 | Aoki et al. |
| 6,395,277 B1 * | 5/2002 | Graham .................. 424/184.1 |
| 6,448,231 B2 | 9/2002 | Graham |
| 6,500,436 B2 | 12/2002 | Donovan |
| 6,623,742 B2 | 9/2003 | Voet |
| 6,683,049 B1 | 1/2004 | Aoki et al. |
| 6,841,156 B2 | 1/2005 | Aoki et al. |
| 6,872,397 B2 | 3/2005 | Aoki et al. |
| 6,887,476 B2 | 5/2005 | Aoki et al. |
| 6,939,852 B2 * | 9/2005 | Graham ...................... 514/12 |
| 6,974,578 B1 | 12/2005 | Aoki et al. |
| 6,986,983 B2 | 1/2006 | Aoki et al. |
| 2001/0018415 A1 | 8/2001 | Aoki et al. |
| 2002/0102275 A1 | 8/2002 | Graham |
| 2003/0118598 A1 | 6/2003 | Hunt |
| 2004/0014663 A1 | 1/2004 | Aoki et al. |
| 2004/0126396 A1 | 7/2004 | Aoki et al. |

(Continued)

FOREIGN PATENT DOCUMENTS

GB 2272697 5/1994

(Continued)

OTHER PUBLICATIONS

Hatheway et al. Botulinum Neurotoxin and Tetanus Toxin, 1989, Academic Press, Inc., Lane L. Simpson, editor, Chapter 1, Bacterial Sources of Clostridial Neurotoxins, pp. 3-24.*

(Continued)

*Primary Examiner*—Jon P Weber
*Assistant Examiner*—Abdel A Mohamed
(74) *Attorney, Agent, or Firm*—Stephen Donovan

(57) ABSTRACT

The invention provides for the use of a presynaptic neurotoxin (for example a bacterial neurotoxin such as botulinum toxin A) for the manufacture of a medicament for the treatment of cerebral palsy in juvenile patients. The juvenile patients are preferably juveniles of up to 6 years in age.

6 Claims, No Drawings

U.S. PATENT DOCUMENTS

| | | | |
|---|---|---|---|
| 2004/0126397 A1 | 7/2004 | Aoki et al. |
| 2004/0151740 A1 | 8/2004 | Aoki et al. |
| 2005/0084504 A1 | 4/2005 | Aoki et al. |
| 2005/0112146 A1 | 5/2005 | Graham |

FOREIGN PATENT DOCUMENTS

| | | |
|---|---|---|
| WO | WO93/05800 | 4/1993 |
| WO | WO94/00081 | 1/1994 |
| WO | WO94/00481 | 1/1994 |
| WO | WO94/15629 | 7/1994 |
| WO | WO94/28922 | 12/1994 |
| WO | WO94/28923 | 12/1994 |
| WO | WO95/17904 | 7/1995 |
| WO | WO95/28171 | 10/1995 |
| WO | WO95/30431 | 11/1995 |

OTHER PUBLICATIONS

Adenis et al., "Treatment of Facial Spasm with Botulinum A Toxin," *J. Fr. Ophthal.*, 1990, 13(5):259-264.
Ambache, "A Further Survey of the Action of *Clostridium botulinum* Toxin Upon Different Types of Autonomic Nerve Fibre," *J. Physiol.*, 1951, 113:1-17.
Ambache, "The peripheral action of *Cl. botulinum toxin," J. Physiol.*, 1949, 108(2):127-141.
Anderson et al., "Botulinum Toxin Treatment of Spasmodic Torticollis," *J. of the Royal Soc. Of Med.*, 1992, 85:524-529.
"Athena files US and Canadian Investigational New Drugs," *Scrip*, Jun. 5, 1992, No. 1724, p. 29.
"Athena Makes a Wise Move," *Med. Advertising News*, Nov. 1992, p. 4.
"Athena Outline Business Strategy," *Marketletter*, Oct. 5, 1992.
Balkan et al., "A five year analysis of botulinum toxin type A injections: some unusual features," *Annals of Ophthalmology*, 1991, 23(9):236-333.
Blasl et al., "Botulinum Neurotoxin A Selectively Cleaves the Synaptic Protein SNAP-25," *Nature*, 1993, 365:160-163.
Berardelli et al., "Botulinum Toxin Treatment in Patients with Focal Dystonia and Hemifacial Spasm. A multicenter study of the Italian Movement Disorder Group," *Neurol. Sci*, 1993, 14:361-367.
Bergmann et al., "Selective Degeneration of Sudomotor Fibers in Ross Sydrome and Successful Treatment of Compensatory Hyperhidrosis with Botulinum Toxin," *Muscle & Nerve*, 1998, 21(12):1790-1793.
Biglan, "Experience with Botulinum A toxin (Oculinum) in the treatment of strabismus," *Contemp. Opth. Forum,* 1987, 5(6): 230-240.
Blitzer et al., "Electromyographic Finding in Focal Laryngeal Dystonia (Spastic Dysphonia)," *Ann. Otol. Rhino. Laryngol.*, 1985, 94:591-594.
Bodde et al., "Transdermal Peptide Delivery," *Biochem. Soc. Trans.*, 1989, 17(5): 943-945.
"BOTOX," 2000, 9 pages [web site].
"Botulinum Toxin for the Treatment of Facial Lines and Wrinkles," 2005, [www.shorelaser.com/BotoxA.html], pp. 1-7.
"Botulinum Toxin may be useful in a range of muscular disorders," *Int. Med. News*, 1991, 15:24(16):36.
Boghen, "Effectiveness of Botulinum Toxin in the Treatment of Spasmodic Torticollis," *Eur. Neurol.*, 1993, 33:199-203.
Borodic et al., "Botulinum B Toxin as an Alternative to Botulinum A Toxin: A Histologic Study," *Ophthal. Plast. Reconstr. Surg.*, 1993, 9(3):182-190.
Borodic et al., "Clinical and scientific aspects of botulinum A toxin," *Ophthalm Clinics of N. America*, 1991, 4(3):491-503.
Boroff et al., "Amino acid analysis of the isolated and purified components from crystalline toxin of *Clostridium botulinum* type A," *Infect. Immun.*, 1970, 2(5):679-680.
Brin, "Interventional Neurology: Treatment of Neurological Conditions with Local Infection of Botulinum Toxin," *Arch. Neurobiol.*, 1991, 54(5):173-189.
Brin et al, "Assessment: The clinical usefulness of Botulinum toxin A in treating neurologic disorders," *Neurology*, 1990, 40: 1332-1336.
Brin et al., "Localized Injections of Botulinum Toxin for the Treatment of Focal Dystonia and Hemifacial Spasm," *Advances in Neurology*, 1988, 50:599-608.
Buckelew, "Fibromyalgia: a rehabilitation approach. A review.," *Am. J of Phy. Med. & Rehab.*, 1989, 68(1):37-42.
Callaway, "Botulinum Toxin Type B: Pharmacology and Biochemistry," *Clinics in Dermatology*, 2004, 22:23-29.
"Cervial Dystonia" [www.fpnotebook.com/NEU151htm]; pp. 1-2 (retrieved Sep. 3, 2003).
Choi et al., "Transdermal delivery of bioactive peptides: the effect of n-decylmethyl sulfoxide, pH, and inhibitors on Enkephalin metabolism and transport," *Pharm. Res.,*, 1990, 7(11): 1099-1106.
Cioffi et al., "Microvasculature of the Anterior Optic Nerve," *Surv. Of Ophthal.*, 1994, 38: S107-S116.
Cohen et al., "Treatment of Focal Dystonias of the Hand with Botulinum Toxin Injection" *Neurology*, 1987, 37:123-124.
Clark, "Cervical Dystonia Following Exposure to High-G Forces," *Aviat. Space Environ. Me.,* 1990, 61: 935-937.
Cosgrove et al., "Botulinum toxin A prevents the developments of contractures in the hereditary spastic mouse model," *Dev. Med. And Child Neurol.*, 1994, 36: 379-385.
Cosgrove et al., "Botulinum toxin in the management of lower limb in cerebral palsy," *Dev. Med. And Child Neurol.*, 1994, 36: 386-396.
Das et al., "Effect of treatment with Botulinum toxin on spasticity," *Postgraduate Medical Journal*, 1989, 65:208-210.
Dasgupta et al., "Purification of *Clostridium botulinum* type A toxin Biochimica," *Biochim. Biophys. Acta.*, 1970, 214(2):343-349.
Dasgupta et al., "Role of a protease in natural activation of *Clostridium botulinum* neurotoxin," *Infect. Immun.*, 1972, 6(4):587-590.
Dasgupta et al., "Separation of toxin and Hemagglutinin from crystalline toxin of *Clostridium botulinum* type A by anion exchange chromatography and determination of their dimensions by gel filtration," *J. Biol. Chem.*, 1969, 243(5):1065-1072.
Dasgupta, "The Structure of Botulinum Neurotoxin," *Botulinum Neurotoxin and Tetanus Toxin*, 1989, pp. 53-67.
Davis et al., "Significant Improvement of Stiff-Person Syndrome After Paraspinal Injection of Botulinum Toxin A," *Movement Disorders*, 1993, 8(3):371-373.
Duane, "Spasmodic Torticollis," *Adv. Neuro.,*, 1988, 49: 135-150.
Dunn et al., *Ophthal*., 1986, 93(4): 470-475.
Dykstra et al., "Treatment of Destrusor-Sphincter Dyssnergia with Botulinum A Toxin: A Double-Blind Study," *Arch. Phys. Med. Rehabil.*, 1990, 71:24-26.
Eames et al., "The effect of Botulinum toxin A on gastrocnemius length: magnitude and duration of response," *Dev. Med and Child Neurol.*, 1999, 41: 226-232.
Elston et al., "Paralytic Strabismus: The Role of Botulinum Toxin," *Br. J. Ophthalmol.*, 1985, 69(12):891-896.
Elston, "Thyroid Eye Disease," *Eye*, 1990, 4 (pt. 4):vii.
Elston et al., "Treatment of strabismus in adults with Botulinum toxin A," *Brit. J. of Ophthal.*, 1985, 69(10):718-724.
Escobar et al., "Myofascial Pain Syndrone," *Orth. Review*, 1987, 16(10):708-713.
Eustis et al., "Botulinum Toxin," *Opthal. Clinics of N. Am.*, 1989, 2(1): 163-172.
Foster, "New Wrinkle on Pain Relief: Re-Engineering Clostridial Neurotoxins for Analgesics," *Drug Discovery Today*, 2005, 10(8):563-569.
Gammon et al., "Botulinum chemodenervation treatment of strabismus," *J. Ped. Ophthal. S.*, 1989, 96(7): 931-934.
Gjerstad et al., "Treatment of Focal Dystonia with Botulinum Toxin," *Tidsskrift for Den Norske Laegeforening*, 1991, 111(21):2637-2639.
Glogau, "Botulinum A Neurotoxin for Axillary Hyperhidrosis," *Dermatol. Surg.*, 1998, 24(8):817-819.
Goodnough et al., "Stabilization of Botulinum Toxin Type A During Lyophilization," *Applied and Environmental Microbiology*, 1992, 58(10):3426-3428.

Greene et al., "Development of Antibodies to Botulinum Toxin Type A in Patients with Torticollis Treated with Injections of Botulinum Toxin Type A," *Botulinum and Tetanus Neurotoxins*, 1993, Plenum Press, pp. 651-654.

Greene et al., "Response to Botulinum Toxin F in Seronegative Botulinum Toxin A-Resistant Patients," *Movement Disorders*, 1996, 11(2):181-184.

Greene et al., "Use of Botulinum Toxin F Injection to Treat Torticollis in Patients with Immunity of Botulinum Toxin A," *Movement Disorders*, 1994, 8(4): 479-483.

Grusser, "Die ersten systematischen Beschreibungen und tierexperiemtellen Untersuchungen des Botulisums," *Sudhoffa Archi.*, 1986, 70(2): 167-186.

Habermann, "Foreword," *Botulinum and Tetanus Neurotoxins*, 1993, Plenum Press, pp. v-ix.

Hambleton, "*Clostridum botulinum* Toxins: a general review of involvement in disease, structure, mode of action and preparation for clinical use," *J. Neurol.*, 1992, 239(1):16-20.

Han et al., "Effect of botulinum toxin A chemodenervation in sensory strabismus," *Journal of Pediatric Ophthalamology and Strabismus*, 2001, 38(2):68-71.

Harper et al., "Frey's Syndrome," *International Journal of Dermatology*, 1986, 25(8):524-526.

Hatheway, "Bacterial Sources of Clostridial Neurotoxins," *Botulinum Neurotoxins and Tetanus Toxin*, 1989, Academic Press, pp. 4-24.

Henesen, "Deadly toxin calms excited muscles," *New Scientist*, 1990, New Science Publications, London, GB, No. 1746, p. 24.

Humphry, "Botulinum Toxin: A New Ally of an old adversary," *BMJ*, 1989, 298:136-137.

Jankovic et al., "Therapeutic uses of Botulinum Toxin," *New England Journal of Medicine*, 1992, 324(17):1186-1191.

Jankovic et al., "Botulinum A toxin for cranial-cervical dystonia: A double-blind, placebo-controlled study," *Neurology*, 1987, 37:616-623.

Jankovic et al., "Clinical Use of Botulinum Toxin," *NIH Consensus Conference, New Eng. J. of Med.*, 1991, 324(17): 1186-1194.

Jankovic et al., "Therapy with Botulinum Toxin," 1994 Marcel Dekker, Inc., p. 76.

Jedynak et al., "Treatment of spasmodic torticollis by local injections of Botulinum toxin," *Rev. Neurol.*, 1990, 146:440-443.

Jenzer et al., "Type B botulism. Report on its mild forms with disorders mainly of the autonomic nervous system," *Schweiz Med Wochenschr*, 1974, 104(19):685-693.

Jost et al., "Efficacy and tolerability of a botulinum toxin type A free of complexing proteins (NT201) compared with commercially available botulinum toxin type A (BOTOX(R)) in healthy volunteers," *J. Neurol. Transm.*, 2005, 112: 905-913.

Kaszynski et al., "Mouse Foot Screen for the Inhibition of Sweating by Anticholinergic Drugs," *The J. of Investi. Derma*, 1974, 62:510-513.

Khalafella et al., "Botulinum Toxin and Sweating," *J. Neurology, Neurosurgery and Psychiatry*, 1994, 57:1437-1438.

Knight, "Botulinum Toxin Types A, B and D Inhibit Catecholamine Secretion from Bovine Adrenal Medullary Cells," *FEBS. Lett.*, 1986, 207(2): 222-226.

Kondo et al., "Modification of the action of pentagastrin on acid secretion by Botulinum toxin" *Experientia*, 1977, 33(6):750-751.

Kohl et al., "Comparison of the effect of Botulinum A BOTOX with highly purified neurotoxin (NT201) in the extensor digitorum brevis muscle test," *Movement Disorders*, 2000, 15:165.

Konstazer et al., "Lokale Injektionsbehandlung mit Botulinum-Toxin a bei schwerer Arm-und Beinspastik," *Der Nervenarzt*, 1993, 64(8):517-523.

Laccourreye et al., "Treatment of Frey's Syndrome in Topical 2% Diphemanil Methylsulfate (Prantal); A Double-Blind Evaluation of 15 Patients," *Laryngoscope*, 1990, 100:651-653.

Liedtke et al., "Transdermal administration of insulin in type II diabetes, Results of a clinical pilot study," *Arneimeittelforschung*, 1990, 40(8): 884-886.

Ludlow et al., "Therapeutic Uses of Type F Botulinum Toxin" *New England Journal of Medicine*, 1992, 326(5):349-350.

Magoon, *Ophthal.*, 1989, 96(7): 931-934.

Magoon, "Botulinum Toxin chemo-denervation for strabismus in infants and children," *J. Ped. Ophthal. S.*, 1984, 21(3): 110-113.

Melling et al., *Eye*, 1988, 2:16-23.

Memin et al., "Traitement de la Spasticite par la Toxine Botulique," *Rev. Neurol.*, 1992, 148(3):212-214.

Mezaki et al., "Combined use of Type A and F Botulinum Toxins for Blepharospasm: A Double-Blind Control Trial," *Movement Disorders*, 1999, 14(6):1017-1020.

Montecucco et al., "Botulinum Neurotoxins: Mechansim of Action and Therapeutic Applications," *Mol. Med. Today*, 1996, 2(10):418-424.

Moyer et al., "Effects of Intramuscular Injection of Botulinum Toxin Type B in Nonhuman Primates; Botulinum and Tetanus Neurotoxins—Neurotransmission and Biomedical Aspects," *Botulinum and Tetanus Neurotoxins-Neurotransmission and Biomedical Aspects*,1993, Bibhuti R. Dasgupta (Ed.) Plenum Press.

Moyer et al., "Botulinum Toxin Type B: Experimental and Clinical Experience; Therapy with Botulinum Toxin," 1994, pp. 71-85.

Naumann et al., "Botulinum Toxin for Focal Hyperhidrosis: Technical Consierations and Improvements in Application," *Brit. J. of Derma.*, 1998, 139:1123-1124.

Naumann et al., "Botulinum Toxin for Palmar Hyperhidrosis," *Lancet*, 1997, 349(9047):252.

Naumann et al., "Focal Hyperhidrosis," *Arch. Dermatol.*, 1998, 134:301-304.

Naver et al., "The Treatment of Focal Hyperhidrosis with Botulinum Toxin," *The Eur. J. of Neur.*, 1997, 4(2):S75-S79.

News Publication: "Marketing Approvals," *Med. World News*, 1990, 31(5): 2.

News Publications: "Porton launches Dysport in UK," *Scrip*, 1991, 1607: 23.

News Publication: "U.S. Food & Drug Administration approves coulinum for strabismus in patients 12 years of age and above and for blepharospasm," *Bin. Vis. Quart*, 1990, 5(2): 61.

Odderson, "Axillary Hyperhidrosis: Treatment with Botulinum Toxin A," *Arch. Phys. Med. Rehab*, 1998, 79:350-352.

Overmyer, "Botulinum Toxin: Poison with a purpose," *Mod. Med.*, 1991, 59: 112-116.

Park et al., "Binding of *Clostridium botulinum* type B toxin to rat brain synaptosome," *Fems. Micro. Lett.*, 1990, 60(3): 243-247.

Poewe et al., "Experience with Botulinum Toxin in Cervical Dystonia; Therapy with Botulinum Toxin," 1994, pp. 267-278.

"Porton Refocuses on Pharmaceuticals," *Scrip*, No. 1871, 10 (vol. 9, No. 1993).

Poungvarin et al., "Two hundred and fifty patients with hemifacial spasm treated with botulinum toxin injection," *J. Med. Assoc. Thai*, 1992, 75(4):199-203.

Price et al., "A Comparative Study of Tear Secretion in Blepharospasm and Hemifacial Spasm Patients Treated with Botulinum Toxin," *Journal of Clinical Neuro-Ophthalmol.*, 1993, 13(1):67-71.

Rader, "Biopharmaceutical Products in the Market," *Biopharma*, 2001, 332:271-274.

Ransom et al., "Enzyme-Linked Immunosorbent Assays (ELISAs) to detect Botulinum Toxins Using High Titer Rabbit Anti-Sera," *Botulinum and Tetanus Neurotoxins*, 1993, Plenum Press, pp. 449-462.

Reichl et al., "Hyperesthesia Associated with Hyperextension Injuries of the Neck," *Injury*, 18(4):234, (1987).

Roggenkamper et al., "Efficacy and safety of a new Botulinum Toxin A free of complexing proteins in the treatment of blepharospasm," *J. Neurol. Transm.*, 2006, 113: 303-312.

Rosenbaum et al., "Verical rectus muscle transposition and Botulinum Toxin (Oculinum) to medical rectus for adbucens palsy," *Arch. Ophthal.*, 1989, 107(6): 820-823.

Ruusuvaara and Setala, "Long-term Treatment of Involuntary Facial Spasms Using Botulinum, Toxin," *Acta Opthal.*, 1990, 68:331-338.

Saga et al., "Secretion of Tears in Patients with Hemifacial Spasm," *Jpn. J. Opthalmor.*, 1990, 34:30-35.

Sanders et al, "Drug delivery systems and routs of administration of peptide and protein drugs," *Eur. J. of Drug. Met. And Pharma*, 1990, 12(2): 95-102.

Sasaki et al., "Effect of pyrrolidone derivatives on lipid membrane and protein conformation as transdermal penetration enhancer," *J. Pharmacobio-Dyn.*, 1990, 13: 468-474.

Sato et al., "Purification and some properties of a proteinase and an esterase released from *Clostridium botulinum* A, B, and F types," *Nippon Saik. Zasshi*, 1973, 28(4): 367-374.

Savino et al., "Hemifacial Spasm treated with Botulinum A toxin injection," *Arch. Ophthalmol.*, 1985, 103(9):1305-1306.

Schantz et al., "Preparation and Characterization of Botulinum Toxin Type A for Human Treatment," *Therapy with Botulinum Toxin*, 1994, pp. 657-659.

Schantz et al., "Properties and use of Botulinum Toxin and other Microbial Neurotoxins in Medicine," *Micro. Reviews*, 1992, 56(1):80-99.

Schantz et al., "Quality of Botulinum Toxin for Human Treatment," *Botulinum and Tetanus Neurotoxins*, 1993, pp. 41-49.

Schantz, "Use of crystalline type A botulinum toxin in medical research," *Biomedical aspects of botulism*, 1981, Academic Press, New York, pp. 143-150.

Schiavo et al., "Botulinum Neurotoxins are Zinc Proteins," *J. Bol. Chem.*, 1992, 267(33)23479-23483.

Schiavo et al., "Tetanus and Botulism Neurotoxins: Isolation and Assay," *Methods Enzymol*, 1995, 248:643-652.

Schnider et al., "Double-Blind Trial of Botulinum A Toxin for the Treatment of Focal Hyperhidrosis of the Palms," *Brit. J. of Derma.*, 1997, 136(4):548-552.

Schwartz, "Circulatory Defects of the Optic Disk and Retina in Ocular Hypertension and High Pressure Open Angle Glaucoma," *Survey of Ophthal.*, 1994, 38.

Scott, "A Clinical Preface," *Botulinum and Tetanus Neurotoxins*, 1993, Plenum Press, pp. 557-558.

Scott et al., "Systemic Toxicity of Botulinum Toxin by Intramuscular Injection in the Monkey," *Movement Disorders*, 1988, 3(4):333-335.

Scott, "Botulinum Toxin Treatment of Strabismus and Blepharospasm, a multiple investigator study," *Proceedings of the 5th meeting of the internat'l strabismological association*, 1986, 483-485.

Scott, "vol. VII Module 12: Botulinum Toxin treatment of strabismus," *Am. Aca. Ophthal.*, 1989, 2:1-11.

Scott et al., *Ophthal.*, 1985, 92(5): 676-683.

Scott et al., "Botulinum treatment of strabismus in children," *Trans. Am. Ophthal. Soc.*, 1990, 87: 174-180, 180-184.

Sellin et al., "Different Effects of Types A and B Botulinum Toxin on Transmitter Release at the Rat Neuromuscular Junction," *Acta. Physiolo. Scand.* 1983, 119:127-133.

Shelley et al., "Botulinum Toxin Therapy for Palmar Hyperhidrosis," *J. of Am. Acad. Of Derma.*, 1998, 32:227-229.

Simpson, "Current Concepts of the Mechanism of Action of Clostridial Neurotoxins," *Botulinum and Tetanus Neurotoxins*, 1993, Plenum Press, New York, pp. 1-15.

Simpson, "The Origin Structure and Pharmacological Activity of Botulinum Toxin," *Pharmacol. Reviews*, 1981, 33(3):155-188.

Simpson, "Clinically Relevant Aspects of the Mechanism of Action of Botulinum Neurotoxin," *Journal of Voice*, 1992, 6(4):358-364.

Simons, "Fibrositis/fibromyalgia: a form of myofascial trigger points?," *Am. J. of Med.*, 1986, 81(3A):93-98.

Snow et al., "Treatment of Spasticity with Botulinum Toxin: A Double-Blind Study" *Annals of Neuorology*, 1990, 28(4):512-515.

Srinivisan et al., "Iontophoresis of polypeptides: effect of ethanol pretreatment of human skin," *J. Pharma. Sci.*, 1990, 79(7).

Stacy et al., "Efficacy of Botulinum toxin type B for treatment of blepharospasm: Report of two cases," *Naunyn-Schmiedeberg's Archives of Pharmacology*, 2002, 365(2):R44.

Stevens et al., "Development and Properties of the secretory response in rat sweat glands: Relationship to the induction of cholinergic function in sweat gland innervation," *Dev. Bio.*, 1987, 123:179-190.

Tang-Liu et al., "Intramuscular Injection of I-botulinum Neurotoxin-Complex Versus I-botulinum-free Neurotoxin: Time course of Tissue Distribution," *Toxicon*, 2003, 42:461-489.

Tonneson et al., "A double blind trial of a 16-hour transdermal nicotine patch in smoking cessation," *New Eng. J. Med.*, 1991, 325(5): 311-315.

Truong et al., "BotB (Botulinum Toxin Type B): Evaluation of Safety and Tolerability in Botulinum Toxin Type A-Resistant Cervical Dystonia Patients (Preliminary Study)," *Movement Disorders*, 1997, 12(5):772-775.

Tse et al., "Preparation and characterization of Homogenous Nerutoxin type a from *Clostridium botulinum*," *Eur. J. Biochem.*, 1982, 122:493-500.

Tsui et al., "A Pilot Study on the use of Botulinum Toxin in Spasmodic Torticollis," *The Canadian Journal of Neuro. Sci.*, 1985, 12(4):314-316.

Tsui et al., "Botulinum Toxin Type B in the Treatment of Cervical Dystonia: A Pilot Study," *Neurology*, 1995, 45(11):2109-2110.

Tsui et al., "Local Treatment Spasmodic Torticollis with Botulim Toxin," *Le Journal Canadien des Sci. Neuro.*, 1987, 14(3):533-535.

U.S. Food & Drug Administration, "List of Orphan Designations and Approvals," 2000, pp. 1, 42-46.

Verhoef et al., "Transport of peptide and protein drugs across biological membranes," *Eur. J. Drug Metab.*, 1990, 15(2): 83-93.

Wagman et al., "Botulinum Type A toxin: properties of a toxic dissociation product," *Arch. Biochem. Biophys.*, 1953, 45:375-383.

Wainwright et al., "Food-Borne Botulinum in Alaska, 1947-1985: Epidemiology and Clinical Findings," *J. Infect. Dis.*, 1988, 157(6):1158-1162.

Wohlfarth et al., "Pharmacokinetic Properties of Different Forumulations of Botulinum Neruotoxin Type A," *Naunyn Schmeideberg's Arch. Pharmacol.*, 2002, 365(supp. 2):R48.

Wright et al., "The Spastic Mouse and the search for an animal model of spasticity in human being," *Clin. Orth. And Related Res.*, 1990, 253: 12-19.

Yakovleff et al., "Indications and use of botulinum toxin in the treatment of spasticity," *Annales de Re. et de Med. Phy.*, 1994, 36(5):359-363.

Zhang et al., "Detection of Botulinum Neurotoxin's Enzymatic Activity of Type A Ghuncha Ambrin," *Faseb J.*, 2004, 18(8).

"The Merck Manual of Diagnosis and Therapy," 1987, pp. 1420-1421, 1449-1551.

National Institutes of Health, "Clinical Use of Botulinum Toxin, Consensus Development Conference Statement," Nov. 12-14, 1990, http://consensus.nih.gov/1990/1990BotulinumToxin083html.htm, pp. 1-18.

\* cited by examiner

BOTULINUM TOXIN NEUROTOXIC COMPONENT FOR TREATING JUVENILE CEREBRAL PALSY

CROSS REFERENCE

This application is a continuation of application Ser. No. 10/976,507, filed Oct. 29, 2004, which is a continuation of application Ser. No. 10/155,280, filed May 22, 2002, now abandoned, which is a continuation of application Ser. No. 08/211,352, filed Jun. 27, 1994, now U.S. Pat. No. 6,395,277, which is a section 371 application from PCT/GB92/01697, filed Sep. 16, 1992, which claims priority to GB 9120306.7, filed Sep. 24, 1991. The entireties of all these prior applications and patent is incorporated herein by reference.

BACKGROUND

The present invention relates to the treatment of cerebral palsy in a juvenile patient and in particular to the promotion of normal muscle growth in a juvenile patient suffering from dynamic contractures caused by cerebral palsy.

Cerebral palsy is a collective name given to a range of conditions caused by brain injury caused at or around the time of birth, or in the first year of an infant's life. The brain injury may be caused, for example, by trauma during delivery. It may also arise through such causes as trauma due to road traffic accidents or meningitis during the first year of life. It has been found that there is an increased risk of cerebral palsy in prematurely born babies and, as a result of the improvements in technology which enable premature babies to be kept alive from a much earlier age, the incidence of cerebral palsy in many countries is actually increasing rather than falling.

Although the brain injury causing cerebral palsy is a non-progressive injury, its effects may change as the sufferer grows older. The largest group of sufferers from cerebral palsy suffer from spastic cerebral palsy.

Spastic cerebral palsy is characterized by dynamic contractures of the muscles which impair or inhibit completely the sufferer's ability to use his or her muscles. Moreover, muscle growth is impaired such that the longitudinal muscles become shorter relative to their associated bones as the infant grows older. Where the leg muscles are affected, the mobility of the sufferer can be severely reduced. Conventional attempts to cure this defect and to restore a measure of normal mobility typically have involved surgical intervention to alter the lengths of the tendons once the state has been reached at which the knee joint can no longer be straightened or the sufferer can only walk on tiptoe.

There remains a need for a treatment which allows the longitudinal muscles to grow normally, thereby removing, or at least minimizing the need to resort to surgical intervention. Moreover, there remains a need for a treatment which can augment surgical intervention to improve the mobility of the sufferer.

A bacterial toxin, botulinum toxin, has been used in the treatment of a number of conditions involving muscular spasm, for example a blepharospasm, spasmodic torticollis (cervical dystonia), oromandibular dystonia and spasmodic dysphonia (laryngeal dystonia). The toxin binds rapidly and strongly to presynaptic cholinergic nerve terminals and inhibits the exocytosis of acetylcholine by decreasing the frequency of acetylcholine release. This results in paralysis, and hence relaxation, of the muscle afflicted by spasm.

The term Botulinum toxin is used herein as a generic term embracing the family of toxins produced by the anaerobic bacterium Clostridium botulinum and, to date, seven immunologically distinct toxins have been identified. These have been given the designations A, B, C, D, E, F and G. For further information concerning the properties of the various botulinum toxins, reference is made to the article by Jankovic & Brin, The New England Journal of Medicine, pp 1186-1194, No. 17, 1991 and to the review by Charles L. Hatheway, Chapter 1 of the book entitled "Botulinum Neurotoxin and Tetanus Toxin" Ed. L. L. Simpson, published by Academic Press Inc., of San Diego, Calif. 1989, the disclosures of which are incorporated herein by reference.

The neurotoxic component of botulinum toxin has a molecular weight of about 150 kilodaltons and is thought to comprise a short polypeptide chain of about 50 kD which is considered to be responsible for the toxic properties of the toxin, and a larger polypeptide chain of about 100 kD which is believed to be necessary to enable the toxin to penetrate the nerve. The "short" and "long" chains are linked together by means of disulphide bridges.

The neurotoxic polypeptide component is present in a complex with non-toxic proteins and haemagglutinins, the molecular weight of the complex being in the region of 900 kD.

Botulinum toxin is obtained commercially by establishing and growing cultures of *C. botulinum* in a fermenter and the harvesting and purifying the fermented mixture in accordance with known techniques.

The "A" form of botulinum toxin is currently available commercially from several sources, for example, from Porton Products Ltd., UK under the tradename "DYSPORT", and from Allergan Inc., Irvine, Calif. under the trade name "OCULINUM."

It has now been found by the present inventor that children suffering from cerebral palsy related dynamic muscle contractures exhibit improvements in function following treatment with a botulinum toxin and that such functional improvements persist when the tone reducing effects of the toxin have worn off.

It has also been found that by administering a botulinum toxin to a juvenile spastic mammal during its grown phase, the consequent reduction in tone of the spastic muscle enables increased longitudinal growth of the muscle to take place.

In a first aspect, the present invention provides a method of treating a juvenile patient suffering from arrested muscle grown arising from the presence of dynamic contractures of the muscle, which method comprises administering to the patient a therapeutically effective amount of substance which blocks the release of synaptic vesicles containing acetylcholine.

The present invention also provides a method of treating a juvenile patient suffering from cerebral palsy, which method comprises administering to the patient a therapeutically effective amount of substance which blocks the release of synaptic vesicles containing acetylcholine.

In a further aspect the invention provides a method of treating a juvenile patient suffering from arrested muscle grown arising from the presence of dynamic contractures of the muscle, which method comprises administering to the patient a therapeutically effective amount of a presynaptic neurotoxin, for example a bacterial neurotoxin such as a botulinum toxin.

In a still further aspect the invention provides a method of eating a juvenile patient suffering from arrested muscle growth due to a cerebral palsy, which method comprises administering a presynaptic neurotoxin (for example a bacterial neurotoxin such as a botulinum toxin) to the patient in a non toxic amount sufficient to reduce muscle tone and promote improved muscle growth.

The botulinum toxin used according to the present invention preferably is Botulinum toxin A. Botulinum toxin A is available commercially from Porton Products Limited, UK, and from Allergan Inc., Irvine, Calif.

Administration of the toxin preferably is by means of intramuscular injection directly into a spastic muscle, in the region of the neuromuscular junction, although alternative types of administration (e.g., sub-cutaneous injection) which can deliver the toxin directly to the affected muscle region may be employed where appropriate. The toxin can be presented as a sterile pyrogen-free aqueous solution or dispersion and as a sterile powder for reconstitution into a sterile solution or dispersion.

Where desired, tonicity adjusting agents such as sodium chloride, glycerol and various sugars can be added. Stabilizers such as human serum albumin may also be included. The formulation may be preserved by means of a suitable pharmaceutically acceptable preservative such as a paraben, although preferably it is unpreserved.

It is preferred that the toxin is formulated in unit dosage form, for example it can be provided as a sterile solution in a vial, or as a vial or sachet containing a lyophilised powder for reconstituting a suitable carrier such as water for injection.

In one embodiment the toxin, e.g., botulinum toxin A is formulated in a solution containing saline and pasteurized human serum albumin, which stabilizes the toxin. The solution is sterile filtered (0.2 micron filter), filled into individual vials and then vacuum dried to give a sterile lyophilised powder. In use, the powder can be reconstituted by the addition of sterile unpreserved normal saline (sodium chloride 0.9% for injection).

In order for the benefits of the invention to be realized, administration of the botulinum toxin should commence before the child has completed its growing period and fixed myostatic contracture has occurred. The benefits of the invention can be maximized by administering the botulinum toxin to the child at an early stage in its growing period, for example before the child reaches the age of six.

The dose of toxin administered to the patient will depend upon the severity of the condition, e.g., the number of muscle groups requiring treatment, the age and size of the patient and the potency of the toxin. The potency of the toxin is expressed as a multiple of the $LD_{50}$ value of the mouse, on "unit" of toxin being defined as being the equivalent amount of toxin that kills 50% of a group of mice. The definition currently used in relation to the product marketed by Porton Products Limited. According to this definition, the potency of the botulinum toxin A available from Porton Products Ltd. is such that one nanogram contains 40 mouse units (units).

Typically, the dose administered to the patient will be up to about 1000 units, for example, up to about 500 units, preferably in the range from about 80 to about 460 units per patient per treatment, although smaller or larger doses may be administered in appropriate circumstances. The potency of botulinum toxin, and its long duration of action means that doses will tend to be administered on an infrequent basis. Ultimately, however, both the quantity of toxin administered, and the frequency of its administration will be at the discretion of the physician responsible for the treatment, and will be commensurate with questions of safety and the effects produced by the toxin.

The invention will now be illustrated in greater detail by reference to the following non-limiting examples which describe the results of clinical studies with botulinum toxin A:

EXAMPLE 1

The Use of Botulinum Toxin A in the Management Children with Cerebral Palsy

Thirty three children suffering from cerebral palsy, having a mean age of seven years and an age range of two to seventeen years, were selected for participation in a clinical study.

The criteria for inclusion in the study were the presence of dynamic contractures interfering with function, without clinical evidence of fixed myostatic contracture. Before entering the study, all children underwent clinical evaluation, physiotherapist's assessment and parental assessment. All ambulatory patients underwent gait analysis using electrogoniometers. The children entering the study were suffering from spastic tetraplegia, diplegia, hemiplegia or monoplegia.

The hamstrings and/or calf muscles of each patient were injected with a sterile solution containing the botulinum toxin A (obtained from Porton Products Limited, UK). Total patient doses ranged from 80 units to 460 units (one unit being equivalent to the murine $LD_{50}$). Before injecting any muscle group, careful consideration was given to the anatomy of the muscle group, the aim being to inject the area with the highest concentration of neuromuscular junctions. Before injecting the muscle, the position of the needle in the muscle was confirmed by putting the muscle through its range of motion and observing the resultant motion of the needle end. General anesthesia, local anesthesia and sedation were used according to the age of the patient, the number of sites to be injected and the particular needs of the patient.

Following injection, it was noted that the onset of effects was complete within thirty-six to seventy-two hours and lasted from six to eighteen weeks. There were no systemic or local side-effects. All but one patient had some reduction in muscle tone; the one failure occurred early in the study and was probably the result of the toxin dosage administered (75 units) being sub-therapeutic. None of the patients developed extensive local hypotonicity. The majority of children had an improvement in function both subjectively and when measured objectively with gait analysis.

Following injection of the calf muscle groups, an assessment was made of the passive dorsiflexion at the ankle. It was found that the younger children displayed a marked improvement in passive dorsiflexion, but that for children over six years there was little improvement.

This was probably due to the dynamic contracture being replaced by a fixed contracture which was unresponsive to any amount of paresis.

Case Study 1

A five year old girl with moderate right hemiplegia underwent gait analysis and, on examination, was found to have dynamic contractures of her calf and hamstrings. Gait analysis recordings of sagittal plan movements (with 95% confidence limits) were made prior to injection and these revealed that throughout the gait cycle, the knee was in excessive flexion. Gait analysis also indicated that she was in equinus throughout the gait cycle.

Following injection, the knee could be extended nearly to neutral during stance and the gait analysis pattern, although still abnormal was much improved. The ankle traces recorded indicated that she was able to dorsiflex her ankle in gait and had developed a normal range of movements.

Gait analysis was also undertaken at four months. At this stage the effects of the toxin has clinically worn off and it was found that the knee flexed to the same extent in swing that it did prior to injection. However, the gain of extension in stance was largely preserved. At the ankle, there was some relapse but there was still a lesser degree of equinus.

Case Study 2

Measurements were made of the maximal extension of the knee in a group of patients who underwent hamstring injection. Prior to injection, they all had some degree of dynamic knee flexion contracture. Four weeks following injection, this showed a highly significant improvement.

However, the one patient who was least affected developed recurvatum at the knee following injection. After this, all patients who had a dynamic knee flexion contracture of less than fifteen degrees were excluded from hamstring injection. Only one local side-effect from the treatment was noted and this was a small subcutaneous haematoma which resolved itself in a few days.

EXAMPLE 2

The Treatment of the Hereditary Spastic Mouse with Botulinum Toxin A

In cerebral palsy there is frequently a failure of muscle growth leading to fixed muscular contracture. This failure has also been demonstrated in the hereditary spastic mouse (Wright J and Rang M The Spastic Mouse and the search for an animal model of spasticity in human beings) Clin. Orthop. 1990, 253, 12-19.

A study has been carried out to ascertain the effect of Botulinum Toxin A on the growth of longitudinal muscle in the spastic mouse compared with normal siblings. Groups of spastic mice at six days old had one calf muscle injected with either 1.2 units of Botulinum Toxin A or normal saline.

The mice were sacrificed at maturity and the hind limbs dissected to allow measurement of the muscle and bones.

In the control group, the spastic mice has a 13% failure of longitudinal muscle growth compared with their normal siblings. However, the muscles of the spastic mice injected with Botulinum had growth identical to that of their normal siblings. There was no difference in growth between normal mice injected with saline or Botulinum.

It can be concluded that the injection of intramuscular Botulinum toxin during the growth period of the hereditary spastic mouse allows normal longitudinal muscle growth to take place and it is believed that this finding may have significance in the management of cerebral palsy.

The invention has been illustrated by reference to Botulinum toxin A but it should be understood that the invention is not limited to the use of this toxin. For example, other Botulinum toxins may be employed. Moreover, other presynaptic neurotoxins (e.g., of bacterial origin) which act in a manner similar to botulinum toxin may also be used. Also, synthetic analogues of the botulinum toxins may be envisaged wherein the 50 kD chain and/or the 100 kD chain are subjected to amino acid insertions, deletions and/or substitutions and, provided that such analogues retain the general type of activity exhibited by Botulinum toxin A, their use in the manner described hereinbefore is embraced by the present invention. The invention is also considered to embrace the use of substances structurally dissimilar to Botulinum toxin A, provided that such substances possess a prolonged ability to inhibit or block release of the synaptic vesicles containing acetylcholine.

I claim:

1. A method for treating cerebral palsy in a juvenile patient, the method comprising the step of administering to the patient a therapeutically effective amount of the neurotoxic component of a botulinum toxin, wherein the neurotoxic component administered to the patient has been purified from a botulinum toxin obtained by fermenting a *Clostridium botulinum*, wherein the botulinum toxin is a botulinum toxin type A.

2. A method for treating cerebral palsy in a juvenile patient, the method comprising the step of administering to the patient a therapeutically effective amount of the neurotoxic component of a single botulinum toxin type, wherein the neurotoxic component administered to the patient has been purified from a single botulinum toxin type obtained by fermenting a *Clostridium botulinum*, wherein the botulinum toxin is a botulinum toxin type A.

3. A method for treating cerebral palsy in a juvenile patient, the method comprising the step of administering to the patient a therapeutically effective amount of the neurotoxic component of only a botulinum toxin type A, wherein the neurotoxic component administered to the patient has been purified from a botulinum toxin type A obtained by fermenting a *Clostridium botulinum*.

4. The methods of claims 1, 2 or 3 wherein the neurotoxic component has a molecular weight of about 150 kilodaltons.

5. The methods of claims 1, 2 or 3 wherein the botulinum toxin obtained by fermenting a *Clostridium botulinum* is a botulinum toxin complex.

6. The methods of claims 1, 2 or 3 wherein the botulinum toxin obtained by fermenting a *Clostridium botulinum* is a botulinum toxin complex with a molecular weight of about 900 kilodaltons.

* * * * *

UNITED STATES PATENT AND TRADEMARK OFFICE
CERTIFICATE OF CORRECTION

PATENT NO. : 7,378,389 B2
APPLICATION NO. : 11/752096
DATED : May 27, 2008
INVENTOR(S) : Herbert Graham It is certified that error appears in the above-identified patent and that said Letters Patent is hereby corrected as shown below:

On page 2, item (56), under "Other Publications", in column 1, line 14, delete "Outline" and insert -- Outlines --, therefor.

On page 2, item (56), under "Other Publications", in column 1, line 17, delete "236" and insert -- 326 --, therefor.

On page 2, item (56), under "Other Publications", in column 1, line 24, delete "Sydrome" and insert -- Syndrome --, therefor.

On page 2, item (56), under "Other Publications", in column 1, line 30, delete "Finding" and insert -- Findings --, therefor.

On page 2, item (56), under "Other Publications", in column 2, line 11, delete ""Cervial" and insert -- "Cervical --, therefor.

On page 2, item (56), under "Other Publications", in column 2, line 22, delete "developments" and insert -- development --, therefor.

On page 2, item (56), under "Other Publications", in column 2, line 29, after "toxin" insert -- , --.

On page 2, item (56), under "Other Publications", in column 2, line 45, delete "Destrusor-Sphincter Dyssnergia" and insert -- Detrusor-Sphincter Dyssynergia --, therefor.

On page 2, item (56), under "Other Publications", in column 2, line 56, delete "Syndrone,"" and insert -- Syndrome," --, therefor.

On page 2, item (56), under "Other Publications", in column 2, line 58, delete "Opthal." and insert -- Ophthal. --, therefor.

On page 3, item (56), under "Other Publications", in column 1, line 8, after "Toxin" insert -- Type --.

On page 3, item (56), under "Other Publications", in column 1, line 9, after "Toxin" insert -- Type --.

On page 3, item (56), under "Other Publications", in column 1, line 12, delete "tierexperiemtellen" and insert -- tierexperimentellen --, therefor.

UNITED STATES PATENT AND TRADEMARK OFFICE
CERTIFICATE OF CORRECTION

PATENT NO. : 7,378,389 B2
APPLICATION NO. : 11/752096
DATED : May 27, 2008
INVENTOR(S) : Herbert Graham It is certified that error appears in the above-identified patent and that said Letters Patent is hereby corrected as shown below:

On page 3, item (56), under "Other Publications", in column 1, line 12, delete "Botulisums,"" and insert -- Botulisms," --, therefor.

On page 3, item (56), under "Other Publications", in column 1, line 16, delete ""Clostridum" and insert -- "Clostridium --, therefor.

On page 3, item (56), under "Other Publications", in column 1, line 20, delete "Ophthalamology" and insert -- Ophthalmology --, therefor.

On page 3, item (56), under "Other Publications", in column 1, line 25, delete "Neurotoxins" and insert -- Neurotoxin --, therefor.

On page 3, item (56), under "Other Publications", in column 1, line 69, delete "Arneimeittelforschung," and insert -- Arzneimittelforschung, --, therefor.

On page 3, item (56), under "Other Publications", in column 2, line 9, delete "Mechansim" and insert -- Mechanism --, therefor.

On page 3, item (56), under "Other Publications", in column 2, line 20, delete "Consierations" and insert -- Considerations --, therefor.

On page 3, item (56), under "Other Publications", in column 2, line 30, delete "Publications:" and insert -- Publication: --, therefor.

On page 3, item (56), under "Other Publications", in column 2, line 33, delete "coulinum" and insert -- oculinum --, therefor.

On page 3, item (56), under "Other Publications", in column 2, line 52, before "Market" insert -- U.S. --.

On page 3, item (56), under "Other Publications", in column 2, line 61, after "Toxin" insert -- Type --.

On page 3, item (56), under "Other Publications", in column 2, line 64, delete "adbucens" and insert -- abducens --, therefor.

On page 3, item (56), under "Other Publications", in column 2, line 67, after "Botulinum" delete ",".

UNITED STATES PATENT AND TRADEMARK OFFICE
CERTIFICATE OF CORRECTION

PATENT NO. : 7,378,389 B2
APPLICATION NO. : 11/752096
DATED : May 27, 2008
INVENTOR(S) : Herbert Graham It is certified that error appears in the above-identified patent and that said Letters Patent is hereby corrected as shown below:

On page 3, item (56), under "Other Publications", in column 2, line 67, delete "Opthal.," and insert -- Ophthal., --, therefor.

On page 3, item (56), under "Other Publications", in column 2, line 69, delete "Opthalmor.," and insert -- Ophthalmol., --, therefor.

On page 4, item (56), under "Other Publications", in column 1, line 20, delete "Bol." and insert -- Biol. --, therefor.

On page 4, item (56), under "Other Publications", in column 1, line 21, delete "267(33)23479-23483." and insert -- 267(33): 23479-23483. --, therefor.

On page 4, item (56), under "Other Publications", in column 1, line 46, delete "Physiolo." and insert -- Physiol. --, therefor.

On page 4, item (56), under "Other Publications", in column 1, line 59, delete "Neuorology," and insert -- Neurology, --, therefor.

On page 4, item (56), under "Other Publications", in column 2, line 21, delete "Nerutoxin" and insert -- Neurotoxin --, therefor.

On page 4, item (56), under "Other Publications", in column 2, line 28, delete "Botulim" and insert -- Botulism --, therefor.

On page 4, item (56), under "Other Publications", in column 2, line 36, delete "Botulinum" and insert -- Botulism --, therefor.

On page 4, item (56), under "Other Publications", in column 2, line 40, delete "Forumulations" and insert -- Formulations --, therefor.

On page 4, item (56), under "Other Publications", in column 2, line 40, delete "Nerutoxin" and insert -- Neurotoxin --, therefor.

On page 4, item (56), under "Other Publications", in column 2, line 43, delete "being,"" and insert -- beings," --, therefor.

UNITED STATES PATENT AND TRADEMARK OFFICE
CERTIFICATE OF CORRECTION

PATENT NO.         : 7,378,389 B2
APPLICATION NO. : 11/752096
DATED                : May 27, 2008
INVENTOR(S)       : Herbert Graham It is certified that error appears in the above-identified patent and that said Letters Patent is hereby corrected as shown below:

In column 1, line 41-52, delete "Spastic cerebral palsy is characterized by dynamic contractures of the muscles which impair or inhibit completely the sufferer's ability to use his or her muscles. Moreover, muscle growth is impaired such that the longitudinal muscles become shorter relative to their associated bones as the infant grows older. Where the leg muscles are affected, the mobility of the sufferer can be severely reduced. Conventional attempts to cure this defect and to restore a measure of normal mobility typically have involved surgical intervention to alter the lengths of the tendons once the state has been reached at which the knee joint can no longer be straightened or the sufferer can only walk on tiptoe." and insert the same on Col. 1, Line 40 (Approx.) after "palsy." as a continuation of the paragraph.

In column 5, line 15-21, delete "However, the one patient who was least affected developed recurvatum at the knee following injection. After this, all patients who had a dynamic knee flexion contracture of less than fifteen degrees were excluded from hamstring injection. Only one local side-effect from the treatment was noted and this was a small subcutaneous haematoma which resolved itself in a few days." and insert the same on Col. 5, Line 14 after "improvement." as a continuation of the Paragraph.

Signed and Sealed this

Twelfth Day of August, 2008

JON W. DUDAS
*Director of the United States Patent and Trademark Office*